United States Patent
Cao et al.

(10) Patent No.: US 11,761,922 B2
(45) Date of Patent: Sep. 19, 2023

(54) METHOD AND SENSOR FOR DETECTING L-ARGININE

(71) Applicant: CHANGSHA UNIVERSITY OF SCIENCE AND TECHNOLOGY, Changsha (CN)

(72) Inventors: Zhong Cao, Changsha (CN); Ningtao Zhou, Changsha (CN); Li Zhou, Changsha (CN); Qin Zhu, Changsha (CN); Jinglin He, Changsha (CN); Zhongliang Xiao, Changsha (CN); Yumin He, Changsha (CN); Zemeng Feng, Changsha (CN); Yulong Yin, Changsha (CN)

(73) Assignee: CHANGSHA UNIVERSITY OF SCIENCE AND TECHNOLOGY, Changsha (CN)

( * ) Notice: Subject to any disclaimer, the term of this patent is extended or adjusted under 35 U.S.C. 154(b) by 519 days.

(21) Appl. No.: 16/969,588

(22) PCT Filed: Dec. 31, 2019

(86) PCT No.: PCT/CN2019/130232
§ 371 (c)(1),
(2) Date: Aug. 13, 2020

(87) PCT Pub. No.: WO2021/004039
PCT Pub. Date: Jan. 14, 2021

(65) Prior Publication Data
US 2023/0101196 A1    Mar. 30, 2023

(30) Foreign Application Priority Data
Jul. 5, 2019   (CN) .......................... 201910604859.6

(51) Int. Cl.
G01N 27/327     (2006.01)
C07K 1/107      (2006.01)
G01N 27/48      (2006.01)

(52) U.S. Cl.
CPC ....... G01N 27/3277 (2013.01); C07K 1/1077 (2013.01); G01N 27/48 (2013.01)

(58) Field of Classification Search
CPC ... G01N 27/3277; G01N 27/48; C01K 1/1077
See application file for complete search history.

(56) References Cited

U.S. PATENT DOCUMENTS

2005/0090649 A1   4/2005 Lombardi et al.

FOREIGN PATENT DOCUMENTS

| CA | 2605026 A1 * | 3/2009 | ............. C07F 17/02 |
| CN | 105445349 A | 3/2016 | |

(Continued)

OTHER PUBLICATIONS

Cold Spring Harbor Protocols—Phosphate-buffered saline (PBS) recipe, 2006, downloaed from http://cshprotocols.cshlp.org/content/2006/1/pdb.rec8247 on Feb. 1, 2023. (Year: 2006).*
EPO computer-generated English language translation DE 19824959 A1, patent published Dec. 16, 1999 (Year: 1999).*
Kitagawa et al., "Molecular of a helical Peptide with a redox Group in the Metal-Molecule-Metal Junction," J. Phys. Chem. B 2005, 109, 13906-13911 (Year: 2005).*

(Continued)

*Primary Examiner* — Alexander S Noguerola
(74) *Attorney, Agent, or Firm* — Bayramoglu Law Offices LLC

(57) ABSTRACT

A method and a sensor for detecting L-arginine are provided. The method includes synthesizing ferrocene-functionalized hexadecapeptide dithiocyclopentane (FC-P16 Peptide), preparing a polypeptide composite membrane-modified electrode (FC-P16 Peptide/AuE), detecting L-Arg and other steps. The results show that the polypeptide composite membrane-modified electrode (FC-P16 Peptide/AuE) exhibits excellent electrochemical response properties to L-Arg. In 10 mmol/L phosphate-buffered saline (PBS, (Continued)

pH=7.4), the DPV response peak current of the polypeptide composite membrane-modified electrode has an excellent linear relationship with the L-Arg concentration of $1.0 \times 10^{-13}$ mol/L to $1.0 \times 10^{-7}$ mol/L, with a detection limit of $1.0 \times 10^{-13}$ mol/L. With prominent reproducibility, repeatability and selectivity, the modified electrode has potential application in life science and nutritional health.

11 Claims, 4 Drawing Sheets

(56) References Cited

FOREIGN PATENT DOCUMENTS

| | | | |
|---|---|---|---|
| CN | 107271511 A | 10/2017 | |
| CN | 107478700 A | 12/2017 | |
| CN | 110220960 A | 9/2019 | |
| CN | 110220961 A | 9/2019 | |
| DE | 19824959 A1 * | 12/1999 | ........... G01N 27/327 |
| JP | H08336399 A | 12/1996 | |

OTHER PUBLICATIONS

Yun et al., Featuring of transient tunneling current by voltage pulse and application to an electrochemical biosensor, Journal of Applied Physics 123, 124902 (2018) (Year: 2018).*

Zhybak M T, Fayura L Y, Boretsky Y R, Gonchar M V, Sibirny A A, Dempsey E, Turner A P F, Korpan Y I. Amperometric L-arginine biosensor based on a novel recombinant arginine deiminase[J]. Microchimica Acta, May 2, 2017, 184: 2679-2686.

Stasyuk N, Smutok O, Gayda G, Vus B, Koval'chuk Y, Gonchar M. Bi-enzyme l-arginine-selective amperometric biosensor based on ammonium-sensing polyaniline-modified electrode[J]. Biosensors & Bioelectronics, May 10, 2012, 37(1): 46-52.

Stasyuk N Y, Gayda G Z, Gonchar M V. L-Arginine-selective microbial amperometric sensor based on recombinant yeast cells over-producing human liver arginase l[J]. Sensors and Actuators B: Chemical, Jul. 7, 2014, 204: 515-521.

Carter Z A, Kataky R. A G-quadruplex aptamer based impedimetric sensor for free lysine and arginine[J]. Sensors and Actuators B: Chemical, 2017, 243: 904-909.

Sheliakina M, Arkhypova V, Soldatkin O, Saiapina O, Akata B, Dzyadevych S. Urease-based ISFET biosensor for arginine determination[J]. Talanta, 2014, 121: 18-23.

* cited by examiner

METHOD AND SENSOR FOR DETECTING L-ARGININE

CROSS REFERENCE TO THE RELATED APPLICATIONS

This application is the national phase entry of International Application No. PCT/CN2019/130232, filed on Dec. 31, 2019, which is based upon and claims priority to Chinese Patent Application No. 201910604859.6, filed on Jul. 5, 2019, the entire contents of which are incorporated herein by reference.

TECHNICAL FIELD

The present invention relates to amino acid detection, and more particularly, to a method and sensor for detecting L-arginine.

BACKGROUND

L-arginine (L-Arg), also known as a proteinogenic amino acid, is an amino acid essential to maintain the growth and development of infants. L-Arg is an intermediate metabolite of the ornithine cycle, which can promote the conversion of ammonia into urea, thereby reducing the ammonia content in blood. L-Arg also plays a role in improving the health of the immune system and protecting against diseases. In the case of physical injuries, if the immune system in the body is at the optimal state, the healing rate of the body can be increased. In general, Arg plays an extremely-important role in wound healing, cell division, and maintaining the charge balance and physiological functions within the body. Therefore, it is of great significance in the fields of life science and nutritional health to develop a method for rapidly and sensitively detecting L-Arg.

Current methods for detecting L-Arg mainly include turbidimetry, spectrophotometry, liquid chromatography (LC), capillary electrophoresis, mass spectrometry (MS), surface plasmon resonance (SPR) and fluorescence analysis. A fluorescent sensor based on diaryl-rhodamine derivatives has been proposed. It has been found that a complex of the fluorescent sensor with $Cu^{2+}$ exhibits the ability to sensitively identify L-Arg with a lower detection limit of 2.2 µmol/L. However, these instrumental analysis methods have disadvantages. The equipment is bulky, expensive and cumbersome to operate. Electrochemical sensors having advantages such as simplicity, high speed and sensitivity, have attracted widespread attention.

A platinum electrode (PANi/Nafion/Pt) based on double enzymes (arginase I and urease) and modified by electroactive polyaniline can be applied to the detection of L-Arg in wine and juice samples, with a lower detection limit of 38 µmol/L. An L-Arg biosensor based on supersaturated human-liver arginase I recombinant yeast cells has also been proposed. This biosensor has advantages, including rapid response (60 s) and a low detection limit (0.085 mmol/L). However, these types of electrochemical sensors for detecting L-Arg all require the participation of enzymes, which limits their application.

More recently, because peptides can be used to simulate various structural and functional characteristics of proteins, electrochemical sensors based on peptides have been applied to the detection of biomolecules, such as proteins and antigens. One such proposed sensor uses ferrocene-functionalized helical peptides to determine the enzymatic activity of prostate-specific antigen (PSA), and the electrochemical measurement principle is that proteolytic cleavage will occur on the electrode surface in the presence of PSA, resulting in a drop in the current signal. This electrode requires a simple preparation method, and has excellent selectivity and a lower detection limit of 0.2 ng/mL. Another proposed method screens heptapeptides exhibiting specificity for bisphenol A (BPA), which are self-assembled on the surface of a gold electrode, and the peak current decreases in response to the increase of the captured BPA molecules, with a linear response range of 1 nM to 5,000 nM and a lower detection limit of 0.7 nM.

Still another proposed detection method fixes Noro-1 peptide on the surface of a gold electrode, which can be applied to the detection of human Norovirus, with prominent reproducibility and stability, and a lower detection limit of 99.8 nM. However, so far, there has been reported no enzyme-free electrochemical sensor for detecting L-Arg based on a peptide composite membrane.

SUMMARY

The present invention is intended to overcome the deficiencies of the prior art, and provides a method and a sensor for detecting L-Arg.

In order to achieve the foregoing objective, the present invention provides the following technical solution:

The method for detecting L-Arg includes the following steps:

(1) synthesis of ferrocene-functionalized hexadecapeptide dithiocyclopentane (FC-P16 Peptide), with a structural formula shown as formula (I):

formula (I)

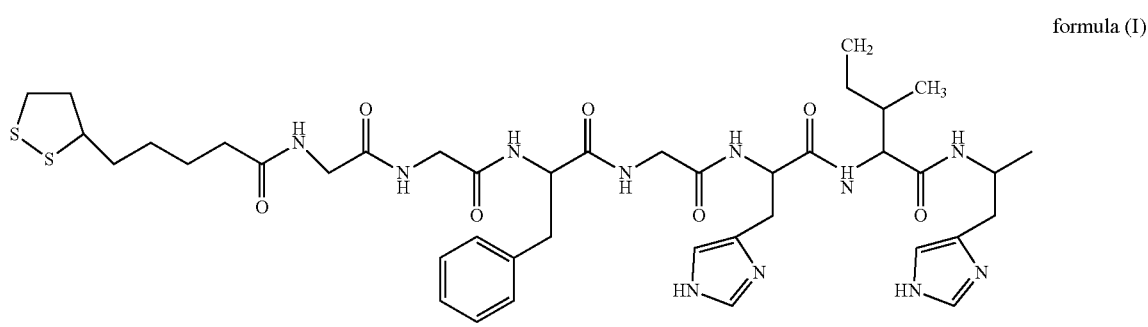

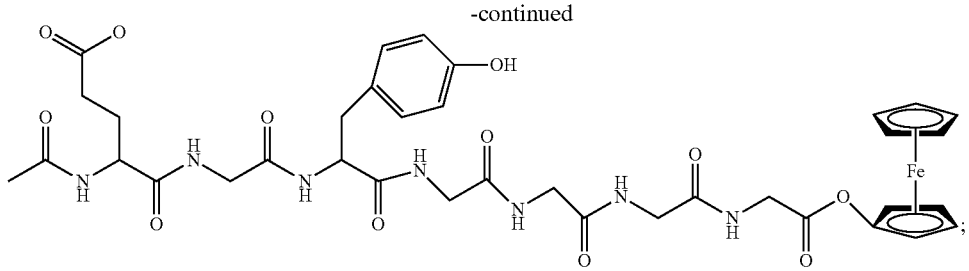
-continued (2) preparation of a polypeptide composite membrane-modified electrode (FC-P16 Peptide/AuE): soaking a gold electrode in Piranha solution, then cleaning, polishing, cleaning, and air drying the gold electrode with $N_2$; soaking the dried electrode in the ferrocene-functionalized hexadecapeptide dithiocyclopentane solution with a concentration of 30 μmol/L to 80 μmol/L and phosphate-buffered saline (PBS, 10 mmol/L, pH=7.4) with a tris(2-carboxyethyl)phosphine (TCEP) concentration of 10 μmol/L to 80 μmol/L for 20 h to 30 h; then soaking the gold electrode in a 6-mercapto-1-hexanol (MCH) solution with a concentration of 0.5 mmol/L to 2.0 mmol/L for 2 min to 30 min; rinsing the gold electrode with PBS along the surface to remove other nonspecifically-adsorbed substances; and air drying the gold electrode with $N_2$ to obtain a polypeptide composite membrane-modified electrode (FC-P16 Peptide/AuE); and (3) constructing a three-electrode system with the polypeptide composite membrane-modified electrode (FC-P16 Peptide/AuE) as a working electrode, a silver/silver chloride electrode as a reference electrode, and a platinum wire electrode as a counter electrode; then investigating the electrochemical behaviors of differently-modified electrodes using cyclic voltammetry (CV) and differential pulse voltammetry (DPV); using the DPV to test L-Arg at different concentrations, and plotting a working standard curve; and then detecting L-Arg in test samples by a known standard addition method.

Preferably, in step (2), the surface of the gold electrode is polished with alumina powders of 1.0 μm, 0.3 μm, and 0.05 μm separately. Preferably, in step (2), the gold electrode has a diameter of 3 mm.

Preferably, in step (3), the electrochemical behaviors of differently-modified electrodes are investigated in 10 mmol/L PBS (pH=7.4), 2.0 mmol/L $[Fe(CN)_6]^{4-3-}$–10 mmol/L PBS, and PBS (10 mmol/L, pH=7.4) with $1.0×10^{-5}$ mol/L L-Arg using CV and DPV; the DPV is adopted to test the relationship between the current response and the concentration for L-Arg at different concentrations, with the following parameters: amplitude: 0.05 V, pulse interval: 0.5 s, sampling width: 0.02, and pulse width: 0.2 s; and the CV is adopted with the following parameters: sampling interval: 0.001 V, and scan rate: 100 mV/s.

The sensor for detecting L-Arg includes a polypeptide composite membrane-modified electrode as a working electrode; the polypeptide composite membrane-modified electrode includes a gold matrix (5); the gold matrix (5) has a surface modified with a polypeptide composite membrane layer (6); the polypeptide composite membrane layer (6) includes polypeptide molecules (7); and the polypeptide molecules (7) are ferrocene-functionalized hexadecapeptide dithiocyclopentane molecules, which have an amino acid sequence shown as GGGGFGHIHEGYGGGG (SEQ ID NO. 2), with -GGGG- at two termini as linkers.

Preferably, the polypeptide composite membrane layer (6) further includes MCH molecules (8).

Preferably, the gold matrix (5) has a thickness of 1.0 mm to 5.0 mm, and the polypeptide composite membrane layer (6) has a thickness of 2 nm to 20 nm.

Preferably, the sensor has an excellent linear relationship with the concentration of L-Arg, with a linear detection range of $1.0×10^{-13}$ to $1.0×10^{-7}$ mol/L, and a detection limit of $1.0×10^{-13}$ mol/L.

In the present invention, L-Arg-specific peptide sequence FGHIHEGY (SEQ ID NO. 1) is first screened, and then based on this sequence, and with -GGGG- at two termini as linkers, a ferrocene-functionalized polypeptide having side chains of FC and 1,2-dithiocyclopentane-3-n-butyl residues at two termini is synthesized, i.e., ferrocene-functionalized hexadecapeptide dithiocyclopentane (FC-P16 Peptide), which has a carbon chain backbone bridge of $-(CH_2)_4-$, and an amino acid sequence shown as SEQ ID NO. 2. This peptide has a disulfide group at the terminus, and the introduction of TCEP results in the breakage of the disulfide bond to form two thiol groups, which can be bonded on the surface of the gold electrode via Au—S bond, thus avoiding the use of any coupling agent. In the present invention, a novel polypeptide composite membrane-modified electrode (namely, FC-P16 Peptide/AuE) is prepared by modifying the surface of a gold electrode with a ferrocene-functionalized polypeptide and using MCH as a sealing agent. CV and DPV are adopted to confirm the formation of a self-assembled monolayer (SAM) from L-Arg-specific peptide molecules on the electrode surface. The experimental results show that the polypeptide composite membrane-modified electrode has an excellent electrochemical response signal to L-Arg, indicating that the polypeptide composite membrane-modified electrode has potential application values in biological sensing and monitoring.

The present invention designs and synthesizes a ferrocene-functionalized hexadecapeptide dithiocyclopentane (FC-P16 Peptide), including an FGHIHEGY amino acid sequence, namely, ferrocene-functionalized hexadecapeptide-3-n-butyl-1,2-dithiocyclopentane (FC-P16-C4-DTCP). The polypeptide molecules are self-assembled on the surface of the gold electrode (AuE) through the reduction of the disulfide bond by TCEP. And the surface of the gold is sealed with MCH to obtain a ferrocene-functionalized polypeptide-modified gold electrode (FC-P16 Peptide/AuE). CV and DPV are adopted to investigate the electrochemical behaviors of L-Arg on differently-modified electrodes, and it is found that FC-P16 Peptide/AuE exhibits excellent electrochemical response characteristics to L-Arg. In 10 mmol/L PBS (pH=7.4), the DPV response peak current of the modified electrode has an excellent linear relationship with the L-Arg concentration of $1.0×10^{-13}$ mol/L to $1.0×10^{-7}$ mol/L, with a detection limit of $1.0×10^{-13}$ mol/L. With prominent reproducibility, repeatability and selectivity, the polypeptide composite membrane-modified electrode has potential application values in life science and nutritional health.

BRIEF DESCRIPTION OF DRAWINGS

In FIG. 1: 1: silver/silver chloride electrode; 2: platinum wire electrode; 3: surface-modified gold electrode; 4: solution to be tested; 5: gold matrix; 6: polypeptide composite membrane layer; 7: polypeptide molecule; 8: MCH molecule; and 9: L-Arg.

DETAILED DESCRIPTION OF THE EMBODIMENTS

In examples, a polypeptide stock solution (1.0 mmol/L) was prepared with ultrapure water (UPW). The polypeptide stock solution, when used, was diluted with PBS (10 mmol/L, pH=7.4) to a desired concentration. 0.20 mol/L NaOH and 0.20 mol/L HCl were used to adjust the pH of PBS. The reagents used were all analytical reagents (AR), and the experimental water was UPW (resistivity≥18.3 MΩ·cm). In the following description, amino acids are described with abbreviations.

I. Experimental Process

1. Preparation of a Polypeptide Composite Membrane-Modified Electrode (FC-P16 Peptide/AuE)

A gold electrode (with a diameter of 3 mm) was soaked in Piranha solution for 5 min, and then washed with UPW. The gold electrode was polished with $Al_2O_3$ powders of 1.0 µm, 0.3 µm and 0.05 µm in sequence to have a mirror surface, then subjected to sonication in UPW, absolute ethanol and UPW separately for 5 min, cleaned, and air dried with $N_2$. At room temperature, the blow-dried gold electrode was soaked in PBS (10 mmol/L, pH=7.4) with 40 µmol/L ferrocene-functionalized hexadecapeptide dithiocyclopentane (FC-P16-C4-DTCP, FC-P16 Peptide) and 50 µmol/L TCEP for 24 h. In order to block the remaining active sites on the surface of the gold and allow the polypeptide to be perpendicular to the surface, the modified electrode was soaked in 1.0 mmol/L MCH solution for 5 min, then rinsed with PBS along the surface of the gold to remove other nonspecifically-adsorbed substances, and air dried with $N_2$ to obtain a polypeptide composite membrane-modified electrode (FC-P16 Peptide/AuE), which was stored at 4° C. for later use.

2. Electrochemical Detection for L-Arg

Figure 1:
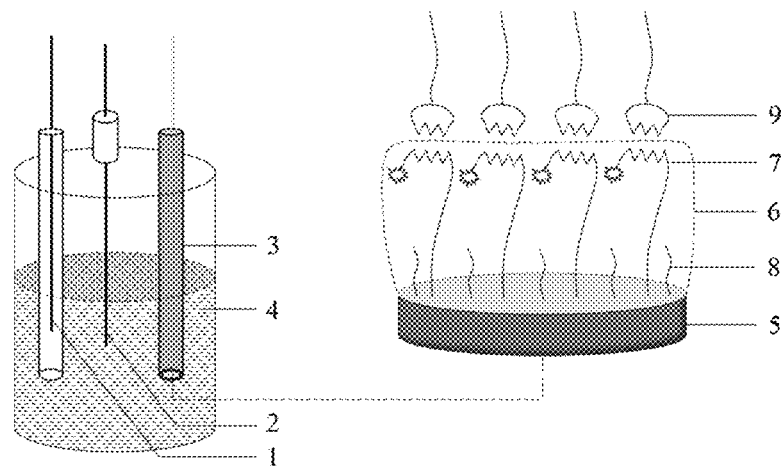
FIG. 1 is a working structural diagram of an L-Arg detection sensor based on a polypeptide composite membrane-modified electrode.
Figure 2:
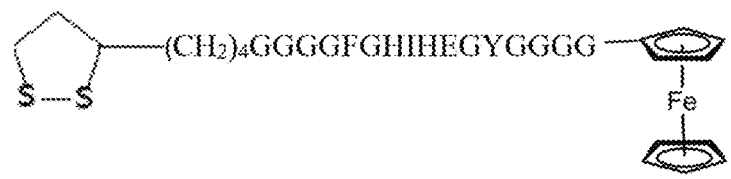
FIG. 2 shows the sequence of ferrocene-functionalized hexadecapeptide dithiocyclopentane (FC-P16-C4-DTCP, FC-P16 Peptide)

Referring to FIG. 1, electrochemical detection was conducted for L-Arg 9 using an electrochemical workstation, a three-electrode system with a surface-modified gold electrode as a working electrode, a silver/silver chloride (saturated potassium chloride) electrode 1 as a reference electrode and a platinum wire electrode 2 as a counter electrode, and 10 mmol/L PBS as a buffer solution. The electrochemical behaviors of differently-modified electrodes were investigated in 10 mmol/L PBS (pH=7.4), 2.0 mmol/L $[Fe(CN)_6]^{4-3-}$–10 mmol/L PBS, and PBS (10 mmol/L, pH=7.4) with $1.0 \times 10^{-5}$ mol/L L-Arg using CV and DPV. The DPV was adopted to test the relationship between the current response and the concentration for L-Arg at different concentrations, and a working standard curve was plotted. The DPV was adopted with the following parameters: amplitude: 0.05 V, pulse interval: 0.5 s, sampling width: 0.02 and pulse width: 0.2 s. The CV was adopted with the following parameters: sampling interval: 0.001 V and scan rate: 100 mV/s.

The surface-modified gold electrode 3 was the polypeptide composite membrane-modified electrode in the sensor for detecting L-Arg of the present invention. The polypeptide composite membrane-modified electrode included a gold matrix 5. The gold matrix 5 had a surface modified with a polypeptide composite membrane layer 6. The polypeptide composite membrane layer 6 included polypeptide molecules 7 and MCH molecules 8. And the polypeptide molecules 7 were ferrocene-functionalized hexadecapeptide dithiocyclopentane molecules (FC-P16 Peptide), namely, ferrocene-functionalized hexadecapeptide-3-n-butyl-1,2-dithiocyclopentane (FC-P16-C4-DTCP), which had an amino acid sequence shown as GGGGFGHIHEGYGGGG with -GGGG- at two termini as linkers. The gold matrix 5 had a thickness of 1.0 mm to 5.0 mm, and the polypeptide composite membrane layer 6 had a thickness of 2 nm to 20 nm.

3. Treatment and Determination for Samples

The standard addition method was adopted to detect L-Arg in pig serum samples (solution 4 to be tested). Pig serum samples (derived from five healthy Duroc×Landrace× Yorkshire piglets, each weighing 7 kg to 15 kg) were provided by the Institute of Subtropical Agriculture, Chinese Academy of Sciences (Changsha). 50.00 µL of each of the five different pig serum samples was diluted 100 times with PBS (4.950 mL) of pH=7.4, and then L-Arg solutions with different concentrations were added to the pig serum solutions. DPV was adopted for determination.

II. Experimental Results and Analysis

1. The Electrochemical Behaviors of L-Arg on the Surface of the Electrode

Figure 3:
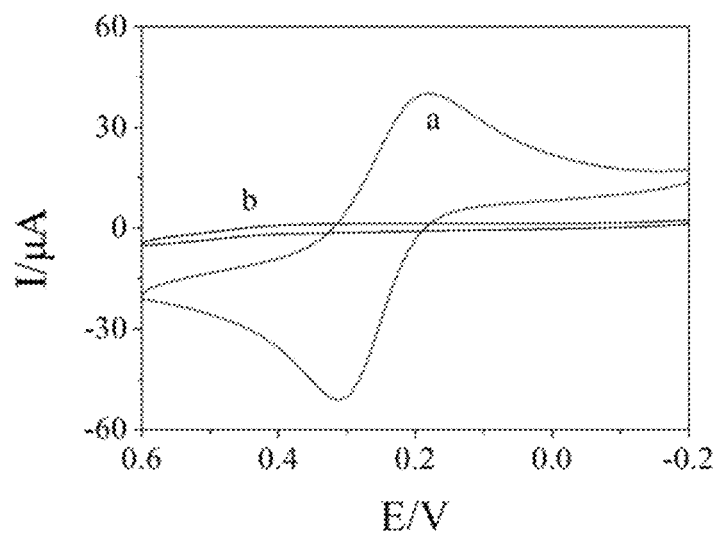
FIG. 3 shows the cyclic voltammogram of differently-modified electrodes in 2.0 mmol/L $[Fe(CN)_6]^{3-}/[Fe(CN)_6]^{4-}$ (at a concentration ratio of 1:1)-PBS (10 mmol/L, pH=7.4), with (a) representing AuE, and (b) representing FC-P16 Peptide/AuE.

The CV and AC impedance method were adopted to observe the assembly of the polypeptide composite membrane-modified electrode. As shown in FIG. 3, it can be found that, in the 2.0 mmol/L $[Fe(CN)_6]^{3-}/[Fe(CN)_6]^{4-}$ (1:1)–10 mmol/L PBS solution, a pair of extremely-distinct oxidation/reduction peaks are observed at the bare gold electrode (AuE, curve a), indicating that there is rapid electron transfer on the bare gold electrode. Compared with the bare gold electrode (AuE), no distinct oxidation/reduction peak is prone to be observed at the FC-P16 Peptide/AuE electrode (curve b). Obviously, after the ferrocene-functionalized hexadecapeptide dithiocyclopentane (FC-P16-C4-DTCP, FC-P16 Peptide) was assembled on the gold electrode, the formed polypeptide composite membrane blocked the electron transfer of the electrode surface to a solution, thereby resulting in a significant decrease in the current value.

Figure 4:
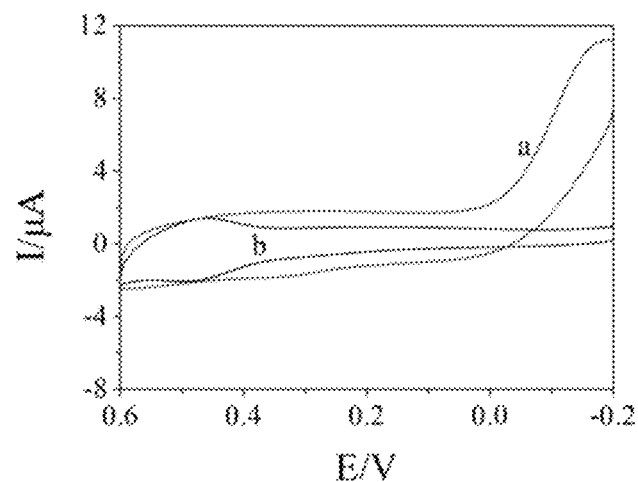
FIG. 4 shows the cyclic voltammogram of AuE (curve a) and FC-P16 Peptide/AuE (curve b) electrodes in PBS (10 mmol/L, pH=7.4), with (a) representing AuE, and (b) representing FC-P16 Peptide/AuE.

Furthermore, the CV behaviors of AuE and FC-P16 Peptide/AuE electrodes were investigated in 10 mmol/L PBS with pH=7.4 (FIG. 4). As shown in FIG. 4, there is no distinct oxidation/reduction peak for AuE (curve a), and the FC-P16 Peptide/AuE (curve b) electrode has a relatively-distinct oxidation/reduction peak at 0.45 V to 0.55 V, indicating that the ferrocene linked to the head of the polypeptide has undergone oxidation-reduction reaction at the interface.

Figure 5A:
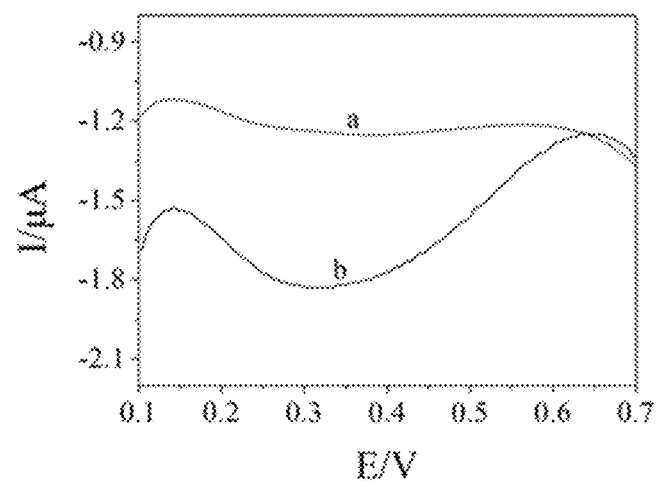
FIG. 5A shows the differential pulse voltammogram of AuE (curve a) and FC-P16 Peptide/AuE (curve b) electrodes in PBS with $1.0 \times 10^{-5}$ mol/L-Arg, with (a) representing AuE, and (b) representing FC-P16 Peptide/AuE.
Figure 5B:
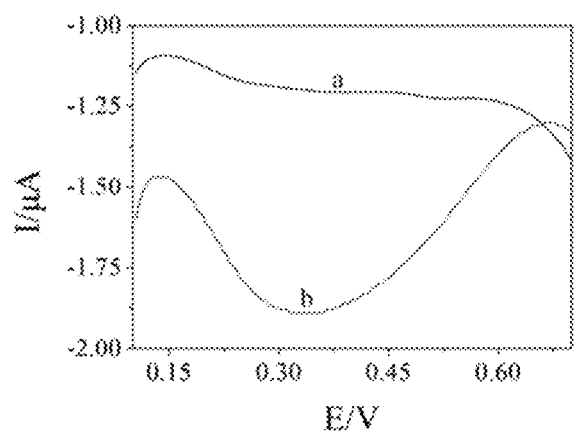
FIG. 5B shows the differential pulse voltammogram of AuE (curve a) and FC-P16 Peptide/AuE (curve b) electrodes in PBS without L-Arg, with (a) representing AuE, and (b) representing FC-P16 Peptide/AuE.

The DPV behaviors of AuE and FC-P16 Peptide/AuE electrodes were investigated in 10 mmol/L PBS with $1.0 \times 10^{-5}$ mol/L-Arg (FIG. 5A) and in PBS without Arg (FIG. 5B). It can be seen from FIG. 5A that the reduction peak of L-Arg on the AuE electrode is not distinct, indicating that L-Arg is difficult to be reduced on the surface of AuE (curve a). Compared with AuE, the FC-P16 Peptide/AuE electrode exhibits a stronger response to L-Arg (curve b), the response peak current is increased, and the peak potential is at $E_p=0.32$ V, indicating that the polypeptide molecules on the FC-P16 Peptide/AuE electrode can well bind L-Arg. In contrast, as shown in FIG. 5B, AuE has no distinct reduction peak in PBS without Arg (curve a), while the FC-P16 Peptide/AuE electrode has a relatively-distinct reduction peak near 0.32 V (curve b), indicating that the ferrocene linked to the head of the polypeptide has undergone reduction reaction at the interface. Therefore, it can be shown that the ferrocene group is linked to the polypeptide molecule.

2. Linear Range and Detection Limit

Figure 6A:
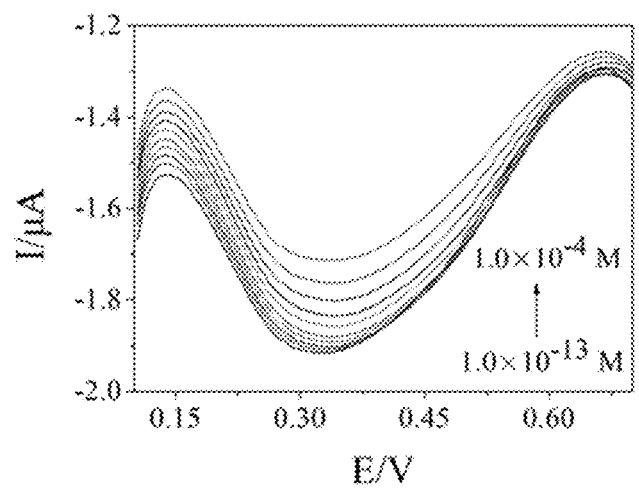
FIG. 6A shows the differential pulse voltammogram of FC-P16 Peptide/AuE responding to different concentrations of L-Arg.
Figure 6B:
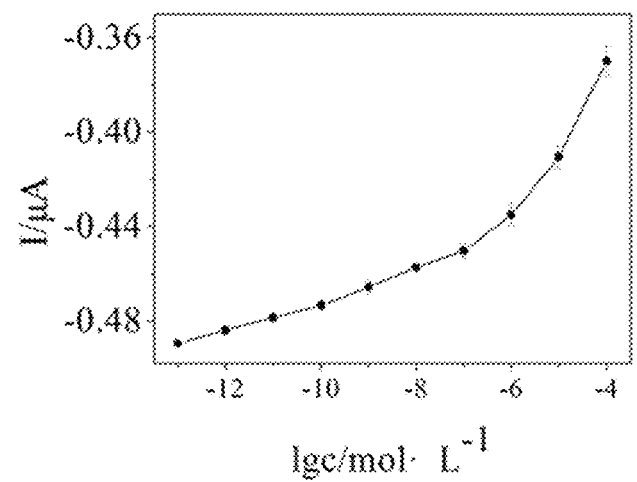
FIG. 6B shows the response relation curve of peak current of FC-P16 Peptide/AuE vs. logarithmic concentration L-Arg.
Figure 6C:
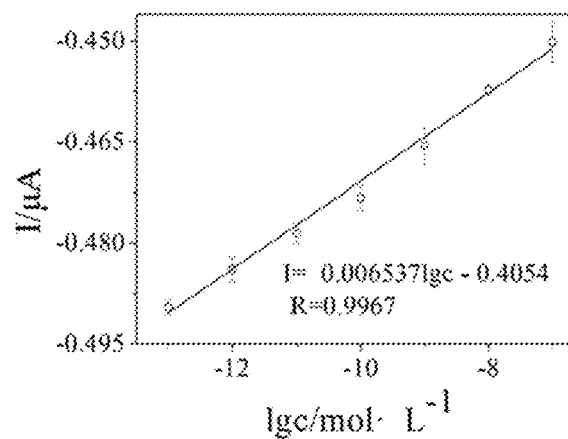
FIG. 6C shows the piecewise linear relationship curve of peak current of FC-P16 Peptide/AuE vs. logarithmic concentration L-Arg.
Figure 6D:
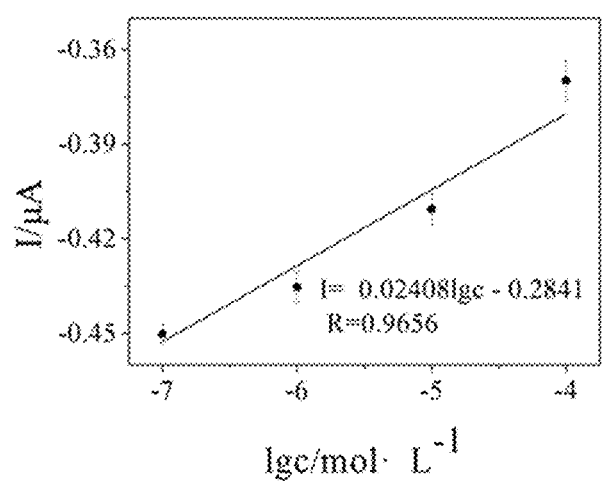
FIG. 6D shows the piecewise linear relationship curve of peak current of FC-P16 Peptide/AuE vs. logarithmic concentration L-Arg.

Under the optimized experimental conditions, the DPV was adopted to detect L-Arg at different concentrations with the FC-P16 Peptide/AuE electrode (FIG. 6A). It can be seen from the figure that, during the process where the concentration of L-Arg is increasing from $1.0 \times 10^{-13}$ mol/L to $1.0 \times 10^{-4}$ mol/L, the response peak current decreases steadily (FIG. 6B), indicating that, as more and more L-Arg molecules are bound to the polypeptide, the steric hindrance between the surface of the gold electrode and the ferrocene is increased, and the electron transfer efficiency is reduced. It can be seen from FIG. 6C that the reduction peak current of L-Arg has an excellent linear relationship with the concentration of L-Arg in the range of $1.0 \times 10^{-13}$ mol/L to $1.0 \times 10^{-7}$ mol/L, with a linear equation of I=0.0065371gc-0.4054, a correlation coefficient of R=0.9967, a lower detection limit of $1.0 \times 10^{-13}$ mol/L. Moreover, it can be seen from FIG. 6D that the reduction peak current of L-Arg has a certain linear correlation with the concentration of L-Arg in the range of $1.0 \times 10^{-7}$ mol/L to $1.0 \times 10^{-4}$ mol/L, with a linear equation of I=0.024081gc-0.2841, and a correlation coefficient of R=0.9656. It can be found that, compared with the L-Arg electrodes reported in other literatures (see Table 1), and especially compared with the enzyme-free electrode, the FC-P16 Peptide/AuE electrode prepared in the present invention has better performance.

TABLE 1

Comparison of performance with different modified electrodes

| Modified electrode | Analyte | Linear range (µmol/L) | LOD (µmol/L) | Reference |
|---|---|---|---|---|
| ADI/PANi/Nafion/Pt-SPE | L-Arg | 3-200 | 1 | [1] |
| U/A/PANi-Nafion/PtE | L-Arg | 70-600 | 38 | [2] |
| U-yeast cells/PANi-Nafion/PtE | L-Arg | 0-600 | 85 | [3] |
| EA#14.3 aptamer/AuE | L-Arg | 0-0.86 | $1.6 \times 10^{-6}$ | [4] |
| Urease-ISFET | L-Arg | 100-2000 | 50 | [5] |
| FC-P16 Peptide/AuE | L-Arg | $1.0 \times 10^{-7}$ to 0.1 | $1.0 \times 10^{-7}$ | This work |

Note:
ADI: arginine deiminase; PANi: Polyaniline; SPE: screen-printed electrode; PtE: Pt electrode; U/A: urease and arginase I; EA#14.3 aptamer: 96 unit thiolated G-quadruples DNA; ISFET: ion-selective field effect transistor.

REFERENCES

[1] Zhybak M T, Fayura L Y, Boretsky Y R, Gonchar M V, Sibirny A A, Dempsey E, Turner A P F, Korpan Y I. Amperometric L-arginine biosensor based on a novel recombinant arginine deiminase[J]. Microchimica Acta, 2017, 184: 2679-2686.

[2] Stasyuk N, Smutok O, Gayda Vus B, Koval'chuk Y, Gonchar M. Bi-enzyme l-arginine-selective amperometric biosensor based on ammonium-sensing polyaniline-modified electrode[J]. Biosensors & Bioelectronics, 2012, 37(1): 46-52.

[3] Stasyuk N Y, Gayda G Z, Gonchar M V. L-Arginine-selective microbial amperometric sensor based on recombinant yeast cells over-producing human liver arginase I[J]. Sensors and Actuators B: Chemical, 2014, 204: 515-521.

[4] Carter Z A, Kataky R. A G-quadruplex aptamer based impedimetric sensor for free lysine and arginine[J]. Sensors and Actuators B: Chemical, 2017, 243: 904-909.

[5] Sheliakina M, Arkhypova V, Soldatkin O, Saiapina O, Akata B, Dzyadevych S. Urease-based ISFET biosensor for arginine determination[J]. Talanta, 2014, 121: 18-23.

4. Reproducibility and Repeatability of Electrodes

Six polypeptide composite membrane-modified electrodes prepared in the same batch under the same conditions were used to detect $1.0 \times 10^{-8}$ mol/L L-Arg, and the relative standard deviation was 2.1%, indicating that the polypeptide-modified electrodes had excellent reproducibility. The same electrode was used to continuously detect $1.0 \times 10^{-8}$ mol/L L-Arg 3 times, and the relative standard deviation was 0.56%, indicating that the electrode had excellent repeatability.

5. Anti-Interference Test

In a three-electrode system with PBS (10 mmol/L, pH=7.4) as the base solution, the effect of common amino acid substances on the detection of L-Arg by the FC-P16 Peptide/AuE-modified electrode was investigated. In the presence of L-Arg ($1.0 \times 10^{-8}$ mol/L), 50-fold concentration of interfering components were added. The results showed that, after methionine (Met), tyrosine (Tyr), isoleucine (Ile), aspartic acid (Asp), glutamine (Gln), leucine (Leu), valine (Val), threonine (Thr), alanine (Ala), phenylalanine (Phe), proline (Pro), histidine (His), glutamate (Glu), glycine (Gly), lysine (Lys) and tryptophan (Trp) were added, the peak current of the modified electrode hardly changed significantly, indicating the FC-P16 Peptide/AuE-modified electrode had excellent selectivity for L-Arg.

In the present invention, an amino acid sequence that can specifically bind L-Arg is designed, a ferrocene probe is introduced, and then a modified electrode based on a ferrocene-functionalized hexadecapeptide composite membrane (FC-P16 Peptide/AuE) is constructed. The polypeptide composite membrane-modified electrode has prominent selectivity, repeatability, reproducibility and low detection limit for L-Arg, and can be applied to the determination of L-Arg in pig serum samples. Therefore, the polypeptide composite membrane-modified electrode has important application prospects in life science and nutritional health.

What is claimed is:

1. A method for detecting L-arginine (L-Arg), comprising the following steps:
   (1) synthesizing a ferrocene-functionalized hexadecapeptide dithiocyclopentane, wherein a structural formula of the ferrocene-functionalized hexadecapeptide dithiocyclopentane is shown as formula (I):

formula (I)

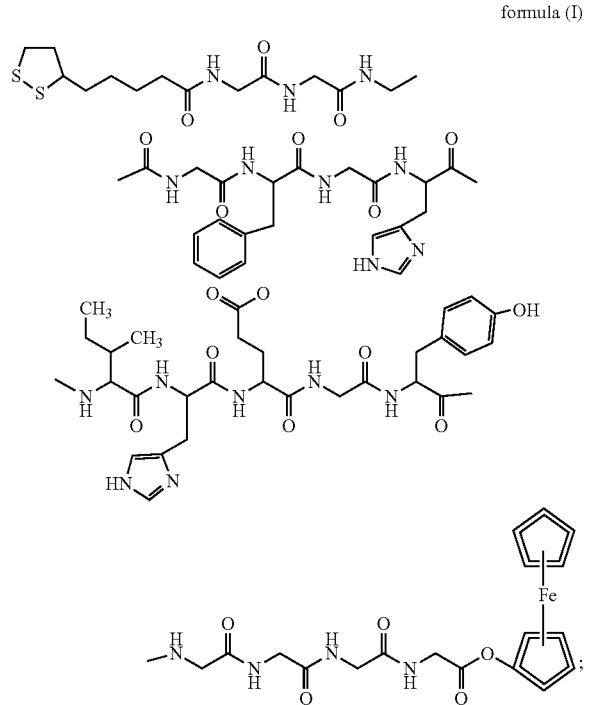

(2) preparing a polypeptide composite membrane-modified electrode, wherein the preparing comprises soaking a gold electrode in a Piranha solution to obtain a first soaked gold electrode, and then cleaning and polishing the first soaked gold electrode to obtain a polished gold electrode, cleaning and air drying the polished gold electrode with $N_2$ to obtain a blow-dried gold electrode; soaking the blow-dried gold electrode in a solution comprising the the ferrocene-functionalized hexadecapeptide dithiocyclopentane and tris(2-carboxyethyl)phosphine (TCEP) in phosphate-buffered saline (PBS) for 20 h to 30 h to obtain a second soaked gold electrode, wherein the concentration of the ferrocene-functionalized hexadecapeptide dithiocyclopentane in the solution is 30 μmol/L to 80 μmol/L and the concentration of TCEP in the solution is 10 μmol/L to 80 μmol/L; then soaking the second soaked gold electrode in a 6-mercapto-1-hexanol (MCH) solution with a MCH concentration of 0.5 mmol/L to 2.0 mmol/L for 2 min to 30 min to obtain a third soaked gold electrode; rinsing the third soaked gold electrode with PBS along a surface of the third soaked gold electrode to remove nonspecifically-adsorbed substances to obtain a cleaned gold electrode; and air drying the cleaned gold electrode with $N_2$ to obtain the polypeptide composite membrane-modified electrode; and (3) constructing a three-electrode system with the polypeptide composite membrane-modified electrode as a working electrode, a silver/silver chloride electrode as a reference electrode, and a platinum wire electrode as a counter electrode; then investigating electrochemical behaviors of the polypeptide composite membrane-modified electrode using cyclic voltammetry (CV) and differential pulse voltammetry (DPV); using the DPV to test L-Arg at different concentrations, and plotting a working standard curve; and then detecting L-Arg in test samples by a standard addition method.

2. The method for detecting the L-arginine (L-Arg) according to claim 1, wherein, in step (2), the polishing is with alumina powders of 1.0 μm, 0.3 μm, and 0.05 μm separately.

3. The method for detecting the L-arginine (L-Arg) according to claim 1, wherein, in step (2), the gold electrode has a diameter of 3 mm.

4. The method for detecting the L-arginine (L-Arg) according to claim 1, wherein, in step (3), the electrochemical behaviors of the polypeptide composite membrane-modified electrode are investigated in PBS, separately in a solution of 2.0 mmol/L $[Fe(CN)_6]^{4-/3-}$, and separately in a solution of $1.0\times10^{-5}$ mol/L L-Arg in PBS using the CV and the DPV; the DPV is adopted to test a relationship between a current response and a concentration of the L-Arg, the DPV is adopted with the following parameters: amplitude: 0.05 V, pulse interval: 0.5 s, sampling width: 0.02, and pulse width: 0.2 s; and the CV is adopted with the following parameters: sampling interval: 0.001 V, and scan rate: 100 mV/s.

5. A sensor for detecting L-Arg, comprising a polypeptide composite membrane-modified electrode as a working electrode; wherein the polypeptide composite membrane-modified electrode comprises gold; the gold has a surface modified with a polypeptide composite membrane layer; the polypeptide composite membrane layer comprises polypeptide molecules; and the polypeptide molecules are ferrocene-functionalized hexadecapeptide dithiocyclopentane molecules.

6. The sensor for detecting the L-Arg according to claim 5, wherein the polypeptide composite membrane layer further comprises MCH molecules.

7. The sensor according to claim 6, wherein the sensor has a, a linear detection range of $1.0\times10^{-13}$ to $1.0\times10^{-7}$ mol/L concentration of L-Arg, and a detection limit of the sensor is $1.0\times 10^{-13}$ mol/L concentration of L-Arg.

8. The sensor for detecting the L-Arg according to claim 5, wherein, the gold matrix has a thickness of 1.0 mm to 5.0 mm, and the polypeptide composite membrane layer has a thickness of 2 nm to 20 nm.

9. The sensor according to claim 8, wherein the sensor has a linear detection range of $1.0 \times 10^{-13}$ to $1.0 \times 10^{-7}$ mol/L concentration of L-Arg, and a detection limit of the sensor is $1.0 \times 10^{-13}$ mol/L concentration of L-Arg.

10. The sensor for detecting the L-Arg according to claim 5, wherein the sensor has a linear detection range of $1.0 \times 10^{-13}$ to $1.0 \times 10^{-7}$ mol/L concentration of L-Arg, and a detection limit of the sensor is $1.0 \times 10^{-13}$ mol/L concentration of L-Arg.

11. A method of using ferrocene-functionalized hexadecapeptide dithiocyclopentane in a preparation of a biosensor, wherein the ferrocene-functionalized hexadecapeptide dithiocyclopentane has a structural formula shown as formula (I):

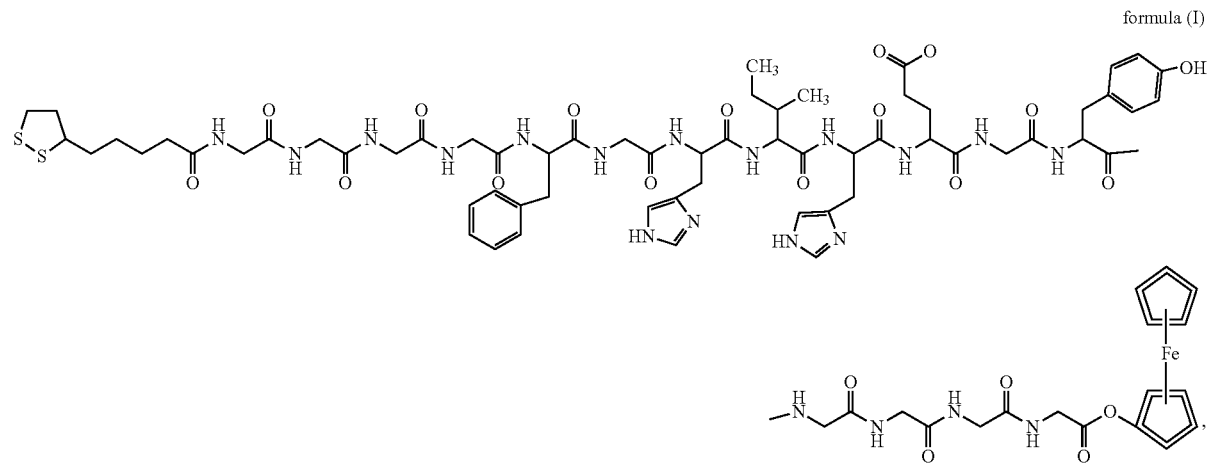

formula (I)

comprising: applying the ferrocene-functionalized hexadecapeptide dithiocyclopentane to an electrode of the biosensor.

* * * * *